United States Patent [19]

Koyamada

[11] 4,313,231
[45] Feb. 2, 1982

[54] VASCULAR PROSTHESIS

[75] Inventor: Kei Koyamada, Morioka, Japan

[73] Assignee: Kabushiki Kaisha Tatebe Seishudo, Tokyo, Japan

[21] Appl. No.: 202,092

[22] Filed: Oct. 30, 1980

[30] Foreign Application Priority Data

Jun. 16, 1980 [JP] Japan .............................. 55-83838[U]

[51] Int. Cl.³ ........................... A61F 1/24; A61F 1/00
[52] U.S. Cl. ..................................... 3/1.4; 128/334 R
[58] Field of Search ..................... 3/1.4, 1; 128/334 R, 128/334 C

[56] References Cited

U.S. PATENT DOCUMENTS 3,657,744 4/1972 Ersek .......................... 128/334 R X
4,190,909 3/1980 Ablaza ..................................... 3/1.4

OTHER PUBLICATIONS

"Crisis: The Acute Dissecting Aneurism" (Leaflet by USCI), The USCI Intraluminal Graft, Jan. 1980, 4 pages.

Primary Examiner—Ronald L. Frinks
Attorney, Agent, or Firm—Ladas & Parry

[57] ABSTRACT

A vascular prosthesis intended principally for use as an intraluminal graft has a flexible tubular main body, a cushioning tube of a flexible, compressible, and suturable Dacron felt secured coaxially to each end of the main body, and two reinforcing rings of stainless steel secured coaxially to opposite ends of each cushioning tube in substantially imbedded state therein, the cushioning tubes at parts thereof between the rings being radially compressible upon being clamped by ligating means, which is thereby prevented from shifting. This prosthesis is particularly effective as an intraluminal graft for surgical treatment of dissecting aortic aneurysm.

5 Claims, 4 Drawing Figures

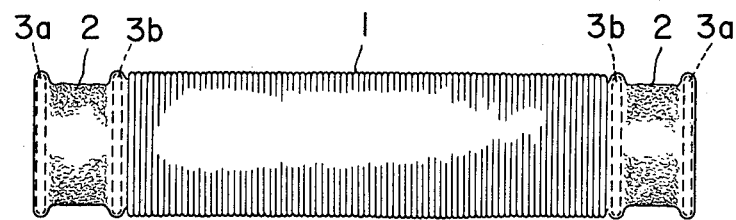
FIG. 1
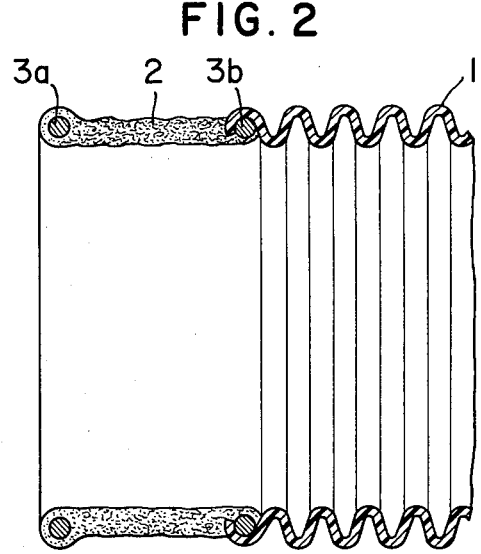
FIG. 2
FIG. 3
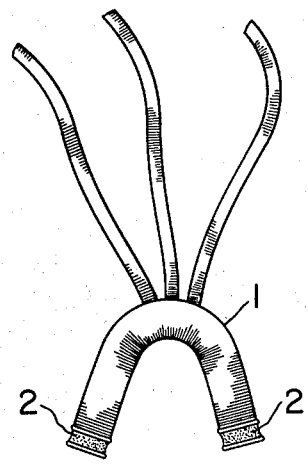
FIG. 4
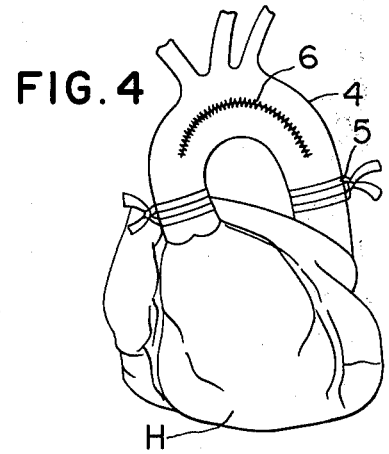

VASCULAR PROSTHESIS

BACKGROUND OF THE INVENTION

This invention relates generally to artificial blood vessel devices and more particularly to improvements in and relating to vascular prostheses including intraluminal grafts for use in surgical operations for treating dissecting aortic aneurysm and the like.

The operation of surgical excision of dissecting aortic aneurysm and replacement with a vascular prosthesis or intraluminal graft is being widely practiced as a standard method of operation. However, the results of this operation cannot by any means be said to be satisfactory. A major reason for this resides in the difficulty of anastomosis or union of the fragile aorta which has dissected and become double walled and a vascular prosthetic device. Hemorrhage from the anastomosed parts prolongs the operative time and may give rise to the death of the patient in many cases.

In view of this circumstance, as a method of carrying out surgical therapy of the instant disease condition safely and, moreover, in a short time, a procedure which comprises inserting an intraluminal graft with a tube of hard Teflon (polytetrafluoroethylene) or stainless steel stitched to each of its two ends intraluminally into the dissecting aorta and tightening the aortic wall around the tubes from outside of the aorta with tapes thereby to fix the aortic wall to the tubes has recently come into practice. In the practice of this method, however, certain difficulties as described below are encountered.

1. In the case where an intraluminal graft with appended tubes of Teflon or stainless steel is ligated with tape or the like at the time of vascular operation as described above, necrosis (gangrene) tends to occur in the blood vessel at the ligated parts because the tubes of Teflon or stainless steel are hard, and when gangrene occurs, there is the risk of rupture of the gangrenous part, which could lead to death.
2. Since the tube parts of a vascular prosthesis with Teflon or stainless-steel tubes at its ends are hard and therefore cannot be compressed, the blood vessel at its part to be operated on must be extensively incised to the length of that artificial graft at the time of the vascular operation. Extensive incision of the blood vessel wall of an aneurism which is in a fragile state entails a great risk and is accompanied by difficulties such as a proportionately large quantity of hemorrhage.

SUMMARY OF THE INVENTION

It is an object of this invention to provide a vascular prosthesis by the use of which the above described problems can be solved or greatly mitigated.

According to this invention, briefly summarized, there is provided a vascular prosthesis comprising a tubular main body of flexible and compressible character, two cushioning tubes of flexible, compressible, and suturable character secured coaxially to respective opposite ends of the main body, and two reinforcing rings of elastic and relatively stiff character secured coaxially to respective opposite ends of each cushioning tube in substantially imbedded state therein, the cushioning tubes at intermediate parts thereof between the reinforcing rings thereof being radially compressible upon being clamped by ligating means, which is thereby prevented from shifting in the axial direction of the prosthesis.

The nature, utility, and further features of this invention will be more clearly apparent from the following detailed description with respect to preferred embodiments of the invention when read in conjunction with the accompanying drawing briefly described below.

BRIEF DESCRIPTION OF THE DRAWINGS

In the drawing:

FIG. 1 is a side view showing an example of a vascular prosthesis according to this invention in its basic form;

FIG. 2 is a fragmentary enlarged view, in longitudinal section, showing the construction of the prosthesis shown in FIG. 1;

FIG. 3 is a side view of another example of a vascular prosthesis according to this invention in form of an intraluminal graft designed for insertion in a diseased aorta; and FIG. 4 is an elevational view indicating an example of use of the intraluminal graft shown in FIG. 3 inserted into the aorta of a human heart.

DETAILED DESCRIPTION OF THE INVENTION

Referring to FIG. 1 the main structure of the vascular prosthesis shown therein is a main body 1 formed by weaving a textile fiber such as Dacron (polyester synthetic fiber), Teflon (polytetrafluoroethylene), or Tetoron (polyester synthetic fiber) into a tubular shape. This main body 1 is provided at each of its two ends with a soft and flexible cushioning material 2 such as Dacron felt also of tubular shape stitched to the main body end. Each end cushioning tube 2 is provided therewith at its ends with elastic and relatively stiff rings 3a and 3b made of a thin metal material such as stainless steel, as best shown in FIG. 2 and secured by stitching to the cushioning tube 2.

When a vascular prosthesis of the above described construction is to be used as an intraluminal graft in the surgical treatment of dissecting aortic aneurysm, it is constructed to assume a form as shown in FIG. 3 of an arch graft. The arch graft of appropriate size is inserted into the aorta 4 of the heart H through a longitudinal incision 6 made therein as shown in FIG. 4, and, after appropriate surgical procedure, the ends of the graft are connected to the aorta 4 by standard ligation technique with a ligature such as pieces of tape 5 made of a material such as Dacron, Teflon or Tetoron. During this ligation, the above mentioned rings 3a and 3b function as reinforcement or support of the soft and flexible graft 1 and prevent it from being squeezed out of shape or collapsing. Thereafter, the incision 6 is closed by suturing.

Because of its construction as described above, the vascular prosthesis according to this invention possesses the following features which are advantageous in comparison with those of known vascular prostheses with solid Teflon or stainless-steel tubes at their ends.

(1) At each end of the vascular prosthesis of this invention, there is secured by stitching, a soft and flexible cushioning material reinforced at its ends by two thin rings instead of a hard tube. For this reason, when the vascular prosthesis is inserted intraluminally as a graft into an aorta and secured thereto by ligation with pieces of tape, there is no danger of necrosis occurring in the aorta at the ligature and possibly causing death.

(2) In the prosthetic state wherein the aorta is tightly ligated with tape relative to the soft and flexible cushioning material between the two rings at each end of the artificial graft, the cushioning material, at its part between the two rings, gives inward because of the clamping pressure from the outer side, whereby the ligating tape becomes fixed between these two rings which are not squeezed and reduced in diameter. Accordingly, the tape at the ligating part cannot shift in position, whereby there is no danger of outward leakage of blood through the joined parts of the aorta and the artificial graft after the ligation.

(3) During a vascular prosthetic operation, the soft and flexible cushioning material at the two end tubes of the vascular prosthesis is readily compressed longitudinally by finger pressure, whereby the graft can be easily inserted through a small incision in the blood vessel. Thus, the danger attendant to a large incision of the vessel wall of a vascular aneurysm which is in a fragile state, as in the case of prior intraluminal grafts, is greatly reduced. As a result: the operation becomes simple; moreover, the hemorrhage quantity is small; the operative time is shortened; the stress load on the patient himself is reduced; and other beneficial results such as rapid post-operative recovery of the patient are afforded.

(4) The tubes of soft and flexible cushioning material at the ends of the main body of the artificial graft are easily penetrated from outside by a suturing needle but are strong enough to hold sutures without tearing, whereby these tubes can be readily used in suturing when necessary. This is a convenient feature which is not possessed by the solid tubes of Teflon or stainless steel at the ends of a known artificial graft. Thus, when necessary, suturing can be carried out through the ligature, the vascular wall, and the end cushioning tubes.

What is claimed is:

1. A vascular prosthesis comprising: a tubular main body of flexible and compressible character; two cushioning tubes of flexible, compressible, and suturable character secured coaxially to respective opposite ends of the main body; and two reinforcing rings of elastic and relatively stiff character secured coaxially to respective opposite ends of each cushioning tube in substantially imbedded state therein, the cushioning tubes at intermediate parts thereof between the reinforcing rings thereof being radially compressible upon being clamped by ligating means, which is thereby prevented from shifting in the axial direction of the prosthesis.

2. A vascular prosthesis according to claim 1 in which the main body is made of a woven synthetic fiber.

3. A vascular prosthesis according to claim 1 or 2 in which the cushioning tubes are made of synthetic fiber felt.

4. A vascular prosthesis according to claim 1 or 2 in which the reinforcing rings are made of stainless steel.

5. A vascular prosthesis according to claim 1 which is formed to have a bent-tube shape of an arch graft with branch tubes communicatively connected thereto and is adapted for use in surgical treatment of dissecting aortic aneurysm.

* * * * *